United States Patent [19]

Widlund et al.

[11] Patent Number: 4,626,254
[45] Date of Patent: Dec. 2, 1986

[54] ABSORBENT ARTICLE

[75] Inventors: Leif U. R. Widlund, Mölnlycke; Carl-Daniel W. Norenberg, Gothenburg, both of Sweden

[73] Assignee: Molnycke AB, Gothenburg, Sweden

[21] Appl. No.: 733,778

[22] Filed: May 14, 1985

[30] Foreign Application Priority Data

May 15, 1984 [SE] Sweden .............................. 8402614

[51] Int. Cl.⁴ .............................................. A61F 13/16
[52] U.S. Cl. .................................. 604/383; 604/385 R
[58] Field of Search ............... 604/378, 380, 382, 383, 604/385, 369, 358

[56] References Cited

U.S. PATENT DOCUMENTS 4,321,924  3/1982  Ahr ..................................... 604/378
4,323,068  4/1982  Aziz .................................... 604/378

Primary Examiner—John D. Yasko
Attorney, Agent, or Firm—Young & Thompson

[57] ABSTRACT

The invention relates to an absorbent article, such as a sanitary towel, diaper or bandage, having an upper layer or topsheet made of a liquid-impermeable material, the topsheet being provided with openings and being intended to lie against the body of the wearer. The invention is mainly characterized in that the openings are located in depressions arranged in the topsheet and in such wall portions of the depressions which, when seen from the mouths of the depressions, form at least a right angle to the plane of the topsheet; and in that the bottoms of the depressions, when projected perpendicularly to the plane of the topsheet, substantially cover the mouths of the depressions in this plane.

9 Claims, 3 Drawing Figures

ABSORBENT ARTICLE

The present invention relates to an absorbent article, such as a sanitary towel, a diaper or bandage, of the kind which comprises a liquid-impermeable upper layer or topsheet which is provided with apertures over at least a part of its area and which is intended to lie against the body of the wearer, and which further comprises an absorbent body located beneath said topsheet.

With absorbent articles of this nature it is of particular importance that the topsheet facing the wearer is dry, even when the article has been worn for an extended period of time.

One serious disadvantage with the majority of such absorbent articles hitherto known to the art is that they are liable to cause chafing of the skin after having been in contact with liquid, such as urine, over long periods of time.

Hitherto, a general solution to this problem has been to use a topsheet or upper layer made from a hydrophobic material, so as to draw moisture from the skin into the absorbent body by suction. It has been found with such absorbents, however, that when the absorbent body is pressed against the wearer, moisture which has earlier been taken up into the absorbent body will penetrate the thin hydrophobic layer and wet the skin of the wearer.

It is true that good insulation between the wearer's skin and an absorbent body can be achieved with a relatively thick, loosely bound fibre-layer. This layer does not conduct liquid, but merely allows it to pass straight through and thus the liquid "falls" right through the fibre-layer and into the absorbent body lying thereagainst. Such insulating layers, however, present problems in manufacture. One such manufacturing problem is that of of bonding the fibre-layer to the topsheet.

In an attempt to provide satisfactory liquid-insulation between the skin of the wearer and the absorbent body, there has been used a topsheet comprising a hydrophobic non-woven material which is embossed so as to increase the volume thereof. One such liquid-insulating absorbent product is described in U.S. Pat. No. 4,041,951. The non-woven layer comprises a large number of downwardly projecting bead-like formations which rest against the planar surface of the absorbent body, while those areas of the non-woven layer which are not depressed when the article is in use, lie against the skin of the wearer. The intention in this respect is to impart to the topsheet sufficient strength to hold the wet absorbent body away from the skin of the user, even when the absorbent article is subjected to high compressive forces during use. One serious drawback with such topsheets is that they are much too stiff and uncomfortable.

The U.S. Pat. No. 3,814,101 describes an absorbent article in which the topsheet comprises a sheet of liquid-impermeable plastics material having a plurality of slits formed therein. The topsheet also has formed therein a large number of depressions or craters. As these depressions are formed, the material located therein, and also the material located therearound, is stretched, so as to widen the slits and permit liquid to pass therethrough. The concept behind this design is that when the absorbent body becomes saturated with body fluid, it will swell and in so doing force the depressions back to a position in which the slits are closed. One drawback with a product of this design, however, is that the number of slits required to provide for satisfactory throughflow of liquid is so numerous that the topsheet is rendered extremely brittle and sensitive to wear. One reason for using a plastics sheet instead of a fibre-layer is to obtain a stronger topsheet. This is obviously not achieved with a slitted plastics sheet. Another inherent disadvantage with an absorbent body produced in accordance with this latter patent is that there is a grave risk of body fluids being unable to pass through the slots and into the absorbent body, and leaking through the sides instead.

U.S. Pat. No. 3,929,135 describes a plastics sheet provided with conical capillaries, which permit liquid to be transferred freely from the user into the absorbent body while preventing flow in the opposite direction at the same time. Because such a topsheet provides a surface which when in contact with the skin of the user is much drier than those topsheets previously used, such a topsheet can be said to constitute a breakthrough in the use of topsheets for absorbent products of the kind in question. The narrower part of respective conical capillaries faces the absorbent body, which results in liquid present in the outer surface of the topsheet being rapidly drawn into the absorbent body by suction, while effectively preventing liquid transfer in the opposite direction at the same time.

The use of such a plastics sheet as the topsheet of an absorbent article, however, requires the total specific area of the throughflow openings (apertures) to be significantly large, so as to obtain a satisfactory throughflow of liquid. As a result of the large number of apertures required, the topsheet becomes transparent and has, inter alia, the negative effect of imparting to the topsheet the appearance of being wet, even though it is dry.

This drawback is particularly manifest when the transparent topsheet which is to face the skin of the wearer forms part of a sanitary towel or a bandage.

Although the topsheet provided with conical capillaries in accordance with U.S. Pat. No. 3,929,135 is superior to all known topsheets with respect to re-wetting of the skin, the topsheet is nevertheless unable to stop re-wetting occurring as a result of the powerful compression forces to which the absorbent article provided therewith is unavoidably subjected during use.

An object of the present invention is therefore to provide a plastics sheet having throughflow openings arranged therein and intended for absorbent articles of the aforesaid kind, which plastic sheet when used as the topsheet or upper layer on said articles provides, in addition to a dry surface against the skin of the wearer, better protection against re-wetting, and which is opaque. To this end the absorbent article according to the invention is characterized in that the apertures are located in respective depressions arranged in the upper layer or topsheet and in such wall portions of said depressions which, when seen from the respective mouths thereof, form at least a right-angle to the plane of the topsheet; and in that the bottoms of said depressions when projected at right angles to said plane substantially cover said mouths of said depressions in said plane.

The invention will now be described in more detail with reference to the accompanying drawings, which illustrate examples of various suitable embodiments of absorbent articles constructed in accordance with the invention. In the drawings, FIG. 1 is a plan view of a sanitary towel provided with a topsheet or upper layer according to the invention;

Figure 1:
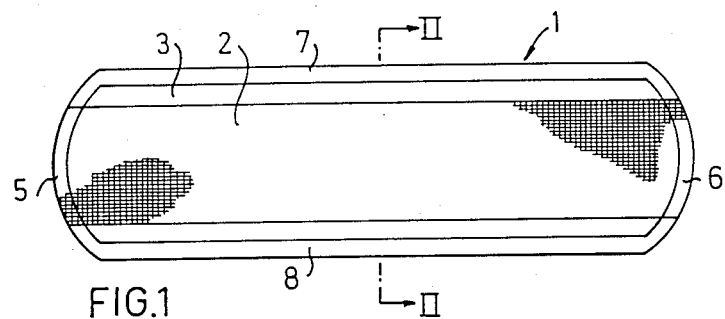

In the sanitary towel illustrated in FIG. 1, only a central region 2 of a topsheet or upper layer 3 of the towel has been provided with apertures for the throughflow of menstrual fluid, said topsheet being intended to face the body of the wearer when the towel is worn. The topsheet 3 is made of plastics film and is joined to a liquid-impermeable plastics-film bottom layer or bottom sheet 4 along the two ends 5,6 of the towel and along the side edges 7,8 thereof, as shown more clearly in FIG. 2. The two outer layers 3,4 enclose therebetween an absorbent body 9, which suitably comprises mechanical or chemical fluff-pulp.

Figure 3:
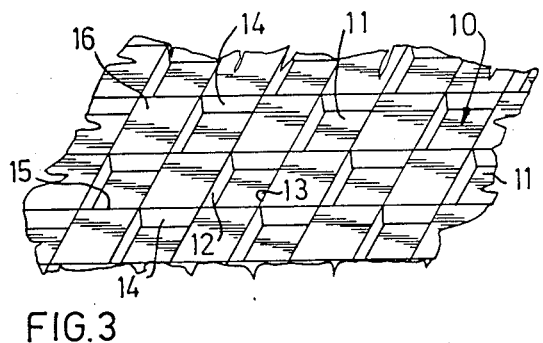
FIG. 3 is a detail view in larger scale, showing the design of the apertures which permit liquid to flow through the topsheet of the towel.

FIG. 3 illustrates the appearance of the upper layer or topsheet 3. Arranged within the central region 2 of this topsheet are depressions or craters 10 of rightangle parallelepipedic configuration. These depressions are defined by a liquid-impermeable bottom 11, two mutually opposing liquid-impermeable sides 12,13 and two mutually opposing open sides 14,15, these latter openings being operative as liquid throughflow openings. As seen in FIG. 3, the topsheet also exhibits smooth, planar areas 16 between the depressions, these areas forming the surface which when the article is used lies against the body of the wearer. Since the apertures or openings are formed in respective walls 14,15 of the depressions and since said walls extend perpendicularly to the actual surface plane of the topsheet, said topsheet will be opaque, provided of course that the material from which the topsheet is made is in itself opaque. One important advantage afforded hereby is that the bottoms of the depressions 10 cover the whole of the respective mouths formed in the plane of the topsheet formed by the intersection of respective depressions with said plane, thereby to completely close said mouths and thereby preventing reverse flow of liquid from the absorption body in a manner to re-wet the skin of the wearer practically completely, even when the absorbent body is subjected to high compressive forces by the body of the wearer.

Another important advantage, afforded by the location of the liquid throughflow openings in planes which are perpendicular to the surface plane lying against the skin of the user, is that air can flow in beneath the depressions in a manner to reach the skin over a relatively large area of the surface lying directly against the skin of the wearer. As a result hereof, the topsheet forming part of an absorbent article made in accordance with the invention and facing the skin of the user can never be experienced as having the nature of a plastics material.

Figure 2:
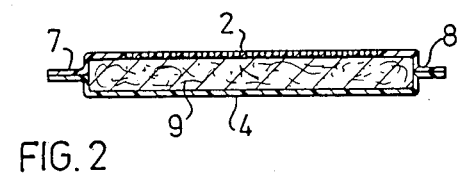
FIG. 2 is a sectioned view of the towel illustrated in FIG. 1, taken on the line II—II in said Figure.

The width of the depressions 10 in the plane of the topsheet 3 is suitably of the order of 0.1–6.0 mm. The width of said depressions is selected in accordance with the body fluid to be absorbed by the product. Although FIGS. 1–3 illustrate embodiments of a sanitary towel constructed in accordance with the invention, it will be understood that the surface material formed in accordance with the invention can also be used with diapers and bandages. The choice of the size of the depressions and the distance at which they are spaced apart is contingent upon the droplet size of the body fluid to be absorbed. In this respect, the interspace between adjacent depressions should not be of such magnitude that droplets can remain lying on the smooth area 16 located between adjacent depressions 10.

The size of the openings 14,15 in the walls of the depressions is suitably in the range of 0.05–2.5 mm. More specifically, the choice of opening-size is made with respect to the width of the depressions in the plane of the topsheet 3 so that liquid droplets reaching the depressions 10 are drawn by suction into the absorbent body 9, through the openings 14,15 located in the depression walls.

Figure 4:
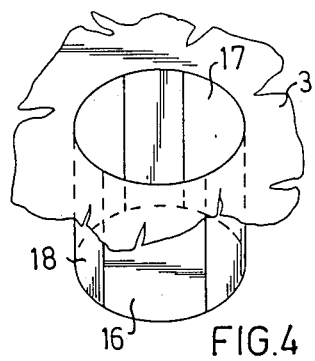
FIGS. 4–9 illustrate further embodiments of throughflow apertures in the topsheet of an absorbent article constructed in accordance with the invention.

FIG. 4 illustrates an alternative embodiment of the depressions illustrated in FIG. 3. The depressions of the FIG. 4 embodiment are cylindrical and have a circular bottom 16. Located in the cylindrical walls are three relatively large holes 17, and of the actual walls of each depression there remains only three strips 18. The check-valve effect of this embodiment has been found particularly effective. The wall strips 18 will give way even when the pressure between the absorbent body and the user is relatively light, thereby to close the mouths of the depressions in the plane of the topsheet 3, with the aid of the bottoms 16, these bottoms readily returning to the original positions immediately the liquid pressure acting from the upper side of the absorbent article exceeds the pressure acting from the absorbent body.

Figure 5:
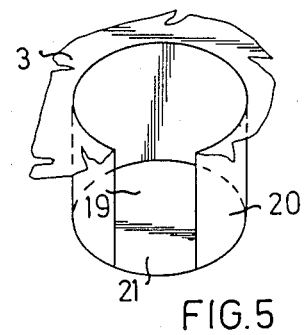

If more rigid cylindrical depressions having a less noticable check-valve effect are desired, the cylindrical walls 20 of the depressions may be provided with a single opening 19, in accordance with the embodiment illustrated in FIG. 5. In this embodiment, the size of a respective bottom 21 coincides with the mouth of a respective depression in the plane of the topsheet or upper layer 3.

Figure 6:
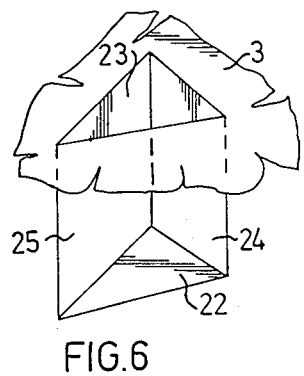

In the embodiment illustrated in FIG. 6, respective depressions are of triangular cross-sectional shape and comprise two walls 23, 24, a through-flow opening 25 and a bottom 22.

Figure 7:
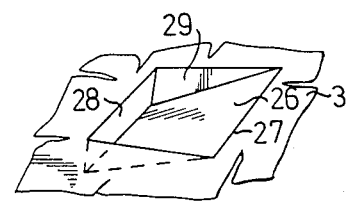

The embodiment of the depressions illustrated in FIG. 7 differs from the previously described embodiments, insomuch as the bottoms 26 of the depressions of this embodiment slope from the upper edge 27 in the plane of the topsheet or upper layer 3 down to the lower edge of a vertical wall opening 28. The depression is given in this way two vertical, triangular walls 29. This embodiment exhibits good check-valve effects.

Figure 8:
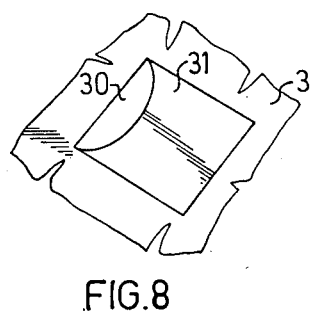

The embodiment illustrated in FIG. 7 can be modified to obtain the embodiment illustrated in FIG. 8, in which latter embodiment the check-valve effect is more pronounced.

In the FIG. 8 embodiment, the vertical opening 30 has the form of a circle segment and the depth of the depression decreases continuously, from the lower edge of the opening towards the opposite end of the depression. In this way, when seen in a plane parallel with the opening 30, the depression has the form of a circle segment. Since the bottom 31 is curved and there are no vertical walls, the check-valve effect produced with this embodiment is particularly pronounced, as before-mentioned.

Figure 9:
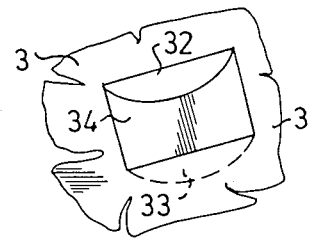

In the embodiment illustrated in FIG. 9, the depression is rectangular in the plane of the topsheet or upper layer 3, and has two mutually opposing, vertical circle-segment shaped wall openings 32,33. The shape of the bottom 34 over the whole of its width coincides with the curvatures of the openings.

As beforementioned when referring to the embodiment illustrated in FIGS. 1-3, the openings in the side walls of the depressions are smaller than the mouths of the depressions in the plane of the topsheet or upper layer 3, thereby to produce a suction effect, by means of which liquid reaching the depressions is drawn into the absorbent body. This suction effect can be further amplified, by applying a thin layer of fibres to the inner surface of the topsheet. These fibres will cross the vertical wall openings of the depressions in a manner to decrease the effective size of said openings, with an increased suction effect as a result thereof.

The aforedescribed plastic topsheet or upper layer provided with depressions and through-passing openings is suitably manufactured by vacuum-forming against a matrix having the desired configuration of the article. In this respect, the openings can be formed, for example, by means of cutting surfaces located on the matrix, or with the aid of a flowing medium directed against the topsheet and matrix.

The invention is not restricted to the aforedescribed embodiments, since a number of modifications can be made within the scope of the following claims.

For example, the walls of respective depressions can be strengthened to withstand large compression forces, i.e. to counter-act the check-valve effect. In this respect, the walls may be strengthened by corrugating said walls or by coating them with reinforcing fibres.

As will be understood, the openings in the depression walls need not extend over the entire height of the respective walls. Instead, the openings may be made to terminate at a distance from the plane of the topsheet or upper layer 3.

In certain conceivable embodiments of the depressions the depressions may lack a true bottom, for example in such depression configurations in which the depression is tubular and in which the longitudinal axis thereof forms an angle other than 90° with the plane of the topsheet and said depressions are open at respective ends. Thus, the term "bottom" used in the following main claim may comprise, either totally or partially, wall portions of the depressions. It will be understood from this that the "bottom" of a depression comprises those wall portions and/or true bottom portions which when projected perpendicularly to the plane of the topsheet or upper layer cover the mouth of respective depression in said plane.

We claim:

1. An absorbent article, such as a sanitary towel, a diaper or bandage, comprising a liquid-impermeable topsheet which is provided with openings over at least part of its area and which is intended to lie against the body of the wearer, and an absorbent body located beneath said topsheet, the openings being arranged in depressions in the topsheet and in such wall portions of said depressions which, when seen from the mouth of the depressions, form at least a right angle to the plane of said topsheet; the bottoms of said depressions, when projected perpendicularly onto the plane of the topsheet, substantially covering the mouths of the depressions in said plane.

2. An article according to claim 1, in which the depression walls extending from the plane of the topsheet to the bottoms of said depressions are so thin and/or have such small width in relation to the opening or openings in said walls that the depressions operate as check valves when the absorbent body is compressed as a result of compression forces occurring during the use of said article.

3. An article according to claim 1 in which the width of the depressions in the plane of the topsheet is in the order of 0.1-6.0 mm; and in that the openings in the walls of said depressions have a height in the order of 0.05-2.5 mm.

4. An article according to claim 1, in which together the depressions constitute between 10 and 70% of the area of the topsheet.

5. An article according to claim 1, in which the depressions have, overall, mutually the same depths; and in that the depression wall or walls is, or are, substantially vertical.

6. An article according to claim 1, in which that each of the depressions has a bottom which extends obliquely upwards, from the lower edge of a wall opening to the plane of the topsheet.

7. An article according to claim 1, in which that each of the depressions has a vertical wall opening in the form of a circle segment; and in that the depth of said depression decreases away from said opening, thereby to provide a recess having a good check valve effect.

8. An article according to any one of claim 1, in which that the depressions are of substantially rectangular configuration in the plane of the topsheet and are provided with two mutually opposing congruent circle segment shaped wall openings and have respective bottoms which coincide, over the whole of their length, with the arcuate curvature of the wall openings.

9. An article according to claim 1, in which that a thin layer of fibres applied to the inner surface of the topsheet, said fibre layer being adapted to amplify the transportation of liquid through the openings of the topsheet and into the absorbent body.

* * * * *